US009827218B2

(12) United States Patent
Martinsen et al.

(10) Patent No.: US 9,827,218 B2
(45) Date of Patent: Nov. 28, 2017

(54) OMEGA-3 FATTY ACID ARTICLES OF MANUFACTURE, AND METHODS AND APPARATUS FOR MAKING SAME

(71) Applicant: AMBO INNOVATIONS, LLC, Osprey, FL (US)

(72) Inventors: Bo Martinsen, Venice, FL (US); Leif Andreas Riege, Gressvik (SE)

(73) Assignee: AMBO INNOVATIONS, LLC, Osprey, FL (US)

( * ) Notice: Subject to any disclaimer, the term of this patent is extended or adjusted under 35 U.S.C. 154(b) by 0 days.

(21) Appl. No.: 15/101,749

(22) PCT Filed: Dec. 4, 2014

(86) PCT No.: PCT/US2014/068528
§ 371 (c)(1),
(2) Date: Jun. 3, 2016

(87) PCT Pub. No.: WO2015/085045
PCT Pub. Date: Jun. 11, 2015

(65) Prior Publication Data
US 2016/0303064 A1    Oct. 20, 2016

Related U.S. Application Data

(60) Provisional application No. 61/913,048, filed on Dec. 6, 2013.

(51) Int. Cl.
*A01N 59/20*    (2006.01)
*A23L 1/28*    (2006.01)
(Continued)

(52) U.S. Cl.
CPC ............. *A61K 31/202* (2013.01); *A23D 9/02* (2013.01); *A23L 33/12* (2016.08); *A61K 31/352* (2013.01);
(Continued)

(58) Field of Classification Search
CPC .. A23D 7/00; A23D 9/007; C11B 1/00; C11B 3/00; C11C 3/00
(Continued)

(56) References Cited

U.S. PATENT DOCUMENTS

| | | | |
|---|---|---|---|
| 2002/0004074 A1 | 1/2002 | Bakal et al. | |
| 2005/0002992 A1* | 1/2005 | McCleary | A23L 33/175 424/439 |
| 2008/0031869 A1 | 2/2008 | Fontaine | |

FOREIGN PATENT DOCUMENTS

| | | |
|---|---|---|
| WO | 2007/116052 A1 | 10/2007 |
| WO | 2008/022199 A2 | 2/2008 |

(Continued)

OTHER PUBLICATIONS

Teixeira et al. (2003) "Melatonin protects against pro-oxidant enzymes and reduces lipid peroxidation in distinct membranes induced by the hydroxyl and ascorbyl radicals and by peroxynitrite," J. Pineal Res. 35(4):262-268.
(Continued)

*Primary Examiner* — Monzer R Chorbaji
(74) *Attorney, Agent, or Firm* — Brian C. Trinque; Gordon R. Moriarty; Lathrop Gage LLP

(57) ABSTRACT

Embodiments of the present invention are directed to methods, apparatus and articles of manufacture that feature omega-3 fatty acids co-processed with flavonoid and lipophilic antioxidants for improved stability.

18 Claims, 3 Drawing Sheets

(51) Int. Cl.

| | |
|---|---|
| *A01N 43/16* | (2006.01) |
| *A61K 31/202* | (2006.01) |
| *C11B 1/10* | (2006.01) |
| *A61K 36/82* | (2006.01) |
| *A61K 36/185* | (2006.01) |
| *A61K 31/352* | (2006.01) |
| *A61K 31/353* | (2006.01) |
| *A61K 31/355* | (2006.01) |
| *A61K 31/593* | (2006.01) |
| *A61K 35/60* | (2006.01) |
| *A23D 9/02* | (2006.01) |
| *C11B 5/00* | (2006.01) |
| *A23L 33/12* | (2016.01) |
| *A61K 31/4045* | (2006.01) |
| *A61K 9/00* | (2006.01) |

(52) U.S. Cl.
CPC .......... *A61K 31/353* (2013.01); *A61K 31/355* (2013.01); *A61K 31/4045* (2013.01); *A61K 31/593* (2013.01); *A61K 35/60* (2013.01); *A61K 36/185* (2013.01); *A61K 36/82* (2013.01); *C11B 1/10* (2013.01); *C11B 5/0085* (2013.01); *C11B 5/0092* (2013.01); *A23V 2002/00* (2013.01); *A61K 9/0053* (2013.01)

(58) Field of Classification Search
USPC ........ 424/638, 745, 757, 464; 514/456, 458; 426/89, 417, 425, 454; 99/485
See application file for complete search history.

(56) References Cited

FOREIGN PATENT DOCUMENTS

| | | | |
|---|---|---|---|
| WO | WO 2008/022199 A2 * | 2/2008 | ............... A23L 1/30 |
| WO | 2008/060163 A1 | 5/2008 | |
| WO | WO 2011/057183 * | 5/2011 | |
| WO | 2014/093313 A1 | 6/2014 | |

OTHER PUBLICATIONS

International Search Report with Written Opinion corresponding to International Patent Application No. PCT/US2014/068528, dated Apr. 9, 2015.

Vural et al. (2001) "Melatonin inhibits lipid peroxidation and stimulates the antioxidant status of diabetic rats," Journal of Pineal Research. 31(3):193-198.

* cited by examiner

OMEGA-3 FATTY ACID ARTICLES OF MANUFACTURE, AND METHODS AND APPARATUS FOR MAKING SAME

RELATED APPLICATIONS

This application is a 35 U.S.C. §371 filing of International Application No. PCT/US2014/068528, filed Dec. 4, 2014, which claims priority to U.S. Provisional Application Ser. No. 61/913,048, filed Dec. 6, 2013, which is incorporated herein by reference in its entirety.

STATEMENT REGARDING FEDERAL FUNDING

Embodiments of the present invention were not conceived or reduced to practice under Federal sponsorship or funding.

FIELD OF THE INVENTION

Embodiments of the present invention relate to medicaments and dietary and food supplements which feature omega-3 fatty acids.

BACKGROUND OF THE INVENTION

Omega-3 fatty acids, as used herein, refers to a family of related compounds with about nine members of which eicosapentaenoic acid (EPA) and docosahexaenoic acid (DHA) are two of the more common. Omega-3 fatty acids have been shown to reduce the risk of heart disease by lowering chronic inflammation and reducing high triglycerides and have a positive effect on children's development when consumed in high enough doses. Omega-3 fatty acids have a positive effect on certain mental illnesses, autoimmune diseases, joint complaints, weight control/fat metabolism and visual acuity. Omega-3 fatty acids are instrumental in a variety of gene expressions.

Despite these positive effects and the suggestion from a number of health organizations that people should increase their intake of omega-3 fatty acids, the average consumption of omega-3 fatty acids is twenty percent of the dosage recommended by the American Heart Association.

One problem associated with omega-3 fatty acids is the off-taste and odor associated with oxidized fatty acids. Oxidized fatty acids, and especially oxidized omega-3s, are thought to be less effective or of no beneficial effect since the oxidation process will create chemical changes to the core properties of molecules. Oxidized fatty acids may be even be harmful. The family of compounds comprising omega-3 fatty acids is complex and is normally derived from natural sources, such as sea plants, algae, or fish oil. As used herein, the term "fish oil" refers to oils derived from marine animal sources and is not intended to limit the source to a particular phyletic group. It is intended to encompass, without limitation, oils derived from fish bodies, livers, intestines, heads, eyes, rows or gonads and krill, anchovy, calamari (octopi), shark or seals.

These oils are difficult to process, store and maintain in non-oxidizing conditions. It would be desirable to have omega-3 fatty acid articles of manufacture that can be used in medicaments and dietary and food supplements that have a low concentration of oxidized fatty acids and will resist oxidation.

SUMMARY OF THE INVENTION

Embodiments of the present invention are directed to articles of manufacture, methods of making such articles and apparatus for making such articles. Articles of manufacture of the present invention are compositional in nature, comprising lipids having a high concentration of omega-3 fatty acids and hydrophilic flavonoids. Embodiments of the present invention feature omega-3 fatty acid from naturally occurring sources, for example, fish and marine animal, plant and algal sources. A further aspect of the article of manufacture further comprises lipophilic anti-oxidants. The flavonoids and antioxidants stabilize and prevent oxidation of the omega-3 fatty acids.

As used herein, the term "flavonoid." refers to a broad group of secondary plant metabolites and includes bioflavonoids, isoflavonoids and neoflavonoids. Bioflavonoids share a flavone molecular structure, isoflavonoids are derived from an isoflavan structure and neoflavonoids have a neoflavonoid structure. All of these structures have three rings in which two rings are heterocycles with one phenyl group extending from differing positions of the heterocycle, One of the positions of the heterocycle ring bearing the phenyl group is oxygen and a second oxygen is present in flavone and neoflavonoid structures.

In one aspect, the present invention features flavonoids derived from one or more of the sources selected from tea, moringa and cacao. For example, the leaves, extracts and powders of such sources are used as a material co-processed with the source materials for the omega-3 fatty acids. The leaves, extracts and powders are sources for one or more flavonoids including, without limitation (−) epicatechin, (−) epicatechin gallate, quercetin and epigallocatechin gallate (EGCG). The hydrophilic flavonoids are present in the article of manufacture in a concentration of between 250 to 10,000 ppm, or 500 to 2,000 ppm, or about 1,000 ppm.

In one aspect, the article of manufacture features one or more of lipophilic anti-oxidants selected from the group consisting of alpha-tocopherol (vitamin E), retinol (vitamin A), carotenoids (astaxanthin, lutein and zeaxanthin) and derivatives and cholecalciferol (vitamin $D_3$) and − derivatives. By way of example, without limitation, vitamin E and derivatives refers to such compounds exhibiting vitamin E-like activity such as alpha, beta, gamma and delta tocopherols and tocotrienols. By way of example without limitation, vitamin D and derivatives refers to such compounds exhibiting vitamin D-like activity such as ergosterol, 7-dehydrocholesterol, ergocalciferol and cholecalciferol. By way of example, without limitation, vitamin A and derivatives refers compounds exhibiting vitamin A-like activity such as retinol, beta carotene and other carotenoids, including, without limitation, astaxanthin lutein and zeaxanthin and various pro-vitamin A compounds.

In one aspect, the article of manufacture features melatonin in an amount sufficient to inhibit the lipid destroying (oxidation) reaction of enzymes released in the manufacturing process. The concentration of melatonin is determined and brought to a predetermined level to produce a standard amount in the refined omega-3 oils.

In one aspect, the article of manufacture features lipophilic antioxidants derived from natural sources. For example, food sources rich in such compounds such as, by way of example without limitation, carrots and high value leafy green vegetables or marine sources like shrimp and shrimp-like animals, by way of example, *Calanus finmarchicus*. Or, the anti-oxidants are obtained from non-natural sources. Embodiments of the present invention feature anti-oxidants added to the source materials for the omega-3 fatty acids and co-processed with the fatty acids. The resulting article of manufacture has lipophilic anti-oxidants present in a concentration of between 250 to 10,000 ppm, or 500 to 2,000 ppm, or about 1,000 ppm.

In one aspect, the article of manufacture is incorporated in a food product, or incorporated in a dosage form for administration as a dietary and/or health supplement or as a medicament. For example, without limitation, the food product, dietary or health supplement, or medicament may comprise an omega-3 fatty acid oil for oral administration in a dosage of about 750 to 4000 mg.

A further embodiment of the present invention is directed to a method of making an omega-3 article of manufacture. The method comprises the steps of combining a source of omega-3 fatty acid having a aqueous component and an oil component with one or more sources of flavonoids prior to or concurrent with separating the water component from the oil component; and, separating the water component from the oil component to form an omega-3 fatty acid fraction. The omega-3 fatty acid fraction is used to form an omega-3 article of manufacture.

One aspect of the present method features omega-3 fatty acid from naturally occurring sources, for example, fish and marine animal, plant and algal sources. The flavonoids stabilize and prevent oxidation of the omega-3 fatty acid. The hydrophilic flavonoids are present in the article of manufacture in a concentration of between 250 to 10,000 ppm, or 500 to 2,000 ppm, or about 1,000 ppm.

One aspect of the present method features the source of flavonoids comprising naturally occurring sources such as, by way of example without limitation, leaves, powders and extracts of green tea, cacao and moringa. The source of flavonoids is combined with the source of omega-3 fatty acids, for example, with whole fish, fish parts plant or algal materials, and/or combined when whole fish, fish parts plant and/or algal materials are rendered into small particles by means of mincing or grinding, and/or combined as the fish, fish parts plant or algal materials are pressed to remove oil and water components, and or combined with the oil and water components.

In one aspect, the method features a step of combining the source of omega-3 fatty acid with one or more lipophilic antioxidants prior to or concurrent with the separating step. In one aspect, the article of manufacture features lipophilic antioxidants derived from natural sources. For example, food sources rich in such compounds such as, by way of example without limitation, carrots and high value green leafy vegetables, shrimp and shrimp-like marine animals or their extracts. Or, the anti-oxidants are obtained from non-natural sources. Embodiments of the present invention feature anti-oxidants added to the source materials for the omega-3 fatty acids and co-processed with the fatty acids. That is, the lipophilic antioxidants are combined with the source of omega-3 fatty acids, for example, combined with whole fish, fish parts, plant or algal materials, and/or combined the as whole fish, fish parts, plant and/or algal materials are rendered into small particles by means of mincing or grinding, and/or combined as the fish, fish parts, plant or algal materials are pressed to remove oil and water components, and or combined with the oil and water components.

The resulting article of manufacture has lipophilic antioxidants present in a concentration of between 250 to 10,000 ppm, or 500 to 2,000 ppm, or about 1,000 ppm.

In one aspect the method further comprises the step of adding an amount of melatonin sufficient to inhibit the lipid destroying (oxidation) reaction caused by the release of enzymes during the mincing, grinding, purification and refining steps. The concentration of melatonin during one or more of these steps is monitored to ensure sufficient levels. The concentration of melatonin in omega-3 oils is set to a predetermined value, allowing the standardization of the ratio of melatonin in omega-3 oils.

In one aspect the method further comprises a step of purifying the omega-3 fraction to form a purified omega-3 fraction. Preferably, the method is performed in a substantially continuous process without intervening freeze and thawing steps or storage. In one aspect the method is performed substantially at temperatures not exceeding about 99 degrees centigrade, and more preferably not greater than 40 degrees centigrade.

A further embodiment of the present invention is directed to an apparatus for forming an omega-3 article of manufacture. The apparatus comprises means for forming a particulate omega-3 material, means for forming an omega-3 fraction, and one or more flavonoid reservoirs. The flavonoid reservoir is in communication with one or more of the means for forming a particulate omega-3 material and means for forming an omega-3 fraction, to place flavonoids and/or melatonin in at least one of the means to allow the omega-3 source material and/or omega-3 fraction to be co-processed with the flavonoids and/or melatonin.

In one aspect, the apparatus further comprises means for forming a separated omega-3 fraction. The means for forming a purified omega-3 fraction is in communication with the flavonoid reservoir to place flavonoids and/or melatonin into the omega-3 fraction prior to or concurrent with the further purification and forming a purified omega-3 fraction. One aspect features monitoring the concentration of melatonin in the omega-3 fractions and adding melatonin to a predetermined concentration to standardize the resultant omega-3 oil fraction.

In one aspect the apparatus is maintained at or operates at a temperature not exceeding 99 degrees centigrade and more preferably not greater than about 40 degrees centigrade.

In one aspect, the means for forming a particulate omega-3 material is in communication with means for forming a omega-3 fraction to pass a particulate omega-3 material to said means for forming an omega-3 fraction in a substantially closed process. Similarly, a preferred apparatus has the means for forming an omega-3 fraction in communication with means for forming a separated omega-3 fraction to pass an omega-3 fraction to the means for forming a purified omega-3 fraction.

A further embodiment of the present apparatus features a means for adding one or more lipophilic anti-oxidants to the omega-3 fraction. One embodiment featured a carotenoid reservoir in communication with one or more means for forming a particulate omega-3 material and means for forming an omega-3 to place carotenoids in at least one of the means to allow the omega-3 source and an omega-3 fraction to be co-processed.

Thus, the apparatus performs the steps in a process to form a purified omega-3 fraction in a continuous manner, in a substantially closed, temperature controlled, environment. Such closed, temperature controlled, environment allows the resultant omega-3 fatty acid article of manufacture be made with consistent potency and substantially free of oxidized fatty acids.

One aspect of the present invention features an apparatus that is mobile or capable of being carried on ships or trucks receiving ships harvesting fish, marine animals, plants or algae for processing and making omega-3 fatty acid articles of manufacture.

These and other features and advantages will be apparent to those skilled in the art upon viewing the figures which are described briefly below and studying the text describing the invention in greater detail that follows.

DETAILED DESCRIPTION OF THE INVENTION

Embodiments of the present invention will be described in detail with respect to an article of manufacture of a compositional nature, comprising omega-3 fatty acids and hydrophilic flavonoids. The flavonoids and antioxidants stabilize and prevent oxidation of the omega-3 fatty acids. The present discussion features the preferred embodiments and the best method of carrying out aspects of the invention with the understanding that the embodiments considered preferred or the best mode may change over time.

Embodiments of the present invention feature omega-3 fatty acid from naturally occurring sources, for example, fish and marine animal, plant and algal sources. Plant sources comprise such plants and plant parts from which olive oil, soybean oil, canola oil, high oleic safflower oil, sunflower seed oil, flaxseed oil, coconut oil, corn oil, cottonseed oil, peanut oil, evening primrose oil borage oil and blackcurrant oil are derived. Fish and marine animal sources comprise such animal and animal parts from which cod liver oil, salmon oil, tuna oil, krill oil, *Calanus finmarcicus* oil, cod oil, herring oil, mackerel oil, anchovy oil, sardine oil menhaden oil and shark liver oil is derived.

As used herein, the term, "melatonin" refers to N-acetyl-5-methoxytryptamine and its isomers. Melatonin is a small ubiquitous molecule that acts as a hormone and anti-oxidant in mammal cells. It is produced throughout the body and found in high concentrations in the gut, liver and bile where it is believed to protect the gastro-intestinal tract from being destroyed by the harsh digestive milieu.

Melatonin is also found in many plants and fish where it is believed to be important companion to lipids to protect them from being oxidized by free radicals. Cod liver is very rich in omega-3 fatty acids. It also contains significant amounts of melatonin and its natural isomers. This can explain why cod liver oil in traditional medicine (before the use of modern industrial production methods) was especially known for an anti-pain or arthritis effect since the melatonin family also has very potent anti-inflammation effects that work in conjunction with the omega-3 oils.

Figure 1A:
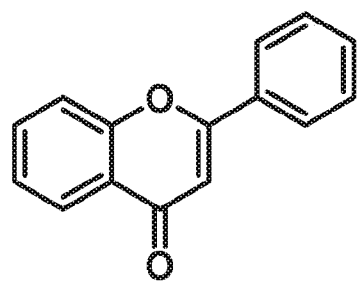
FIGS. 1a, 1b and 1c depict the chemical structure of bioflavonoids, isoflavonoids and neoflavonoids, respectively.
Figure 1B:
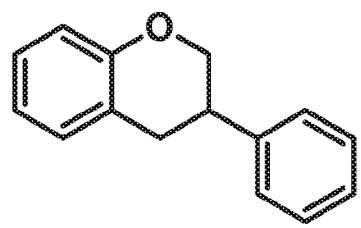
Figure 1C:
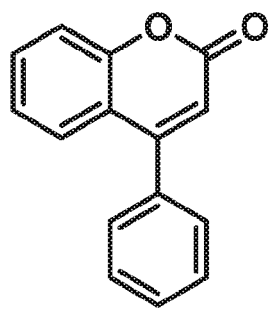

As defined herein the term "flavonoid" refers to a broad group of secondary plant metabolites and includes bioflavonoids, isoflavonoids and neoflavonoids. Bioflavonoids share a flavone molecular structure as depicted in FIG. 1a. Isoflavonoids are derived from an isoflavan structure as best seen in FIG. 1b. Neoflavonoids have a neoflavonoid structure as depicted in FIG. 1c. These structures have three rings in which two rings are heterocycles with one phenyl group extending from differing positions of the heterocycle. One of the positions of the heterocycle ring bearing the phenyl group is oxygen and a second oxygen is present in flavone and neoflavonoid structures.

The present invention features flavonoids derived from one or more of the sources selected from tea, moringa and cacao. For example, the leaves, extracts and powders of such sources are used as a material co-processed with the source materials for the omega-3 fatty acids. The leaves, extracts and powders are sources for one or more flavonoids including, without limitation (−) epicatechin, (−) epicatechin gallate, quercetin and epigallocatechin gallate (EGCG).

As another aspect of the present invention, the article of manufacture comprises omega-3 fatty acids and hydrophilic flavonoids and lipophilic antioxidants, for example carotenoids.

The leaves extracts and powders are co-processed in the sense that the source materials for the omega-3 fatty acids and the source materials for the flavonoids are combined and mixed. For example, without limitation, turning now to FIG. 2, an apparatus for forming an omega-3 article of manufacture, generally designated by the numeral 11 is depicted.

The apparatus 11 comprises the following major elements, means for receiving sources of omega-3 fatty acids 15, means for forming a particulate omega-3 material 17, means for forming a omega-3 fraction 19, and means for separating the omega-3 fatty acid fraction 21, omega-3 fatty acid flavonoid storage means 23 and flavonoid reservoir 25.

The means for receiving sources of omega-3 fatty acids 15 may take several forms and comprise a reservoir, hopper, container, vessel or the like for holding, by way of example, fish and fish parts. This discussion will use the term means for receiving sources of omega-3 fatty acids and hopper 15 interchangeably. The hopper 15 is in communication with means for forming a particulate omega-3 material 17.

As used herein, the term "communicate" and "in communication with" refers to connected to for material transfer, by means of a conveyor belt, auger, conduit or other means known in the art. Communication between hopper 15 and means for forming a particulate omega-3 material 17 is depicted by the conduit 29a.

Means for forming a particulate omega-3 material 17 is, where the material is fish, fish parts, or other plant or animal materials, one or more mincers, cutters and/or grinders, in a suitable container. Those skilled in the art will recognize that features of the hopper 15 can be incorporated into the means for forming a particulate omega-3 material 17. That is, the means 17 and the hopper 15 can be a single unitary structure. This discussion will refer to the means for forming a particulate omega-3 material 17 interchangeably with the term, mincer.

Mincer 17 is in communication with means for forming an omega-3 fraction 19 via conduit 29b. Means for forming an omega-3 fraction 19 comprise, by way of example, without limitation, presses, dissolution and or solubilizers, which release the liquid fractions form the cellular solids. Such means for forming an omega-3 fraction are contained in a suitable vessel. This discussion will refer to means for forming an omega-3 fraction 19 interchangeably with the term press 19.

Press 19 is in communication via conduit 29c with means for separating an omega-3 fraction 21. Means for separating an omega-3 fraction 21 is a vessel for receiving the liquids produced from the press 19. The liquid comprises an aqueous fraction and an oil fraction, which oil fraction comprises in whole or in part, omega-3 fatty acids. The aqueous fraction and oil fractions separate and the oil fraction is removed via conduit 29d to a storage vessel 23. Aqueous fractions are removed via an exit port 31.

Storage vessel 23 may comprise individual product containers for finished omega-3 fatty acids or larger vessels holding omega-3 fatty acids for further processing and/or refinement.

The flavonoid reservoir 25 is in communication with one or more of the means for receiving omega-3 source material 15, means for forming a particulate omega-3 material 17, means for forming an omega-3 fraction 19, and means for separating an omega-3 fraction 21 via conduits 35a, 35b, 35c and 35d. The source material for the flavonoids, for example, without limitation, leaves and other plant material from tea, moringa and/or cacao are stored in the reservoir 25. The flavonoid reservoir 25 places flavonoids in at least one of the means 15, 17, 19, and 21 to allow the omega source material and/or omega-3 fraction to be co-processed with the flavonoids. The flavonoid reservoir 25 may also be placed in communication via conduits and the like [not shown] with the storage vessel 23.

In one embodiment the flavonoids are added to the means for receiving an omega-3 source material 15 and co-processed through mincing. That is, the flavonoid materials are minced and ground with the omega-3 source material to form a particulate admixture. This admixture is processed through pressing carrying forward the flavonoids in the liquid. The liquid is processed through fractionation and separation of fractions. And, each individual step of mincing, pressing, fractionation and separation can be supplemented with added flavonoid source material as the materials move through the apparatus 11.

During the first stage of rendering of fish oil, the fish tissue is crushed and there is a subsequent massive liberation of enzymes that start decomposing the lipids. Melatonin, when in sufficient amounts, can inhibit this lipid destroying (oxidation) reaction. Apparatus 11 has means for monitoring [not shown] and adjusting levels of melatonin during refining. That is, melatonin is added to the flavonoid reservoir 25, or the apparatus comprises a separate melatonin reservoir and metering pump [not shown] or the melatonin is added through the lipophilic anti-oxidant reservoir to be described more fully below.

Present day fish oil refining methods use acid/alkali washing, organic chemicals and high heat which diminish the oil's natural content of melatonin and its isomers making the oil less nutrient rich and also more susceptible to oxidation. The present invention avoids these melatonin depleting steps and the nutrient content monitoring system also allows for adjusting the melatonin level throughout the refining. The finished oil will have a standardized melatonin level that reflects or enhances the fish oil's basal value. Since omega-3 to melatonin ratio is believed to be important for fish oils' therapeutic effects, the present invention allows for standardizing this ratio in the finished oil independently of the specie's original ratio or starting values. For example, without limitation one would monitor the concentration of melatonin and adjust the level of fish parts and the like to greater than 800 picogram melatonin per gram of tissue. With respect to liquids released from such fish parts, one would monitor the concentration of melatonin in such liquids and adjust to a level of 30,000 picogram melatonin per milliliter of liquid.

One embodiment of the apparatus 11 further comprises a lipophilic antioxidant reservoir [not shown]. Lipophilic anti-oxidants may, by way of example, without limitation, comprise members of carotenoid family like astaxanthin extract from krill or Calanus finmarchicus or lutein or beta carotenes from plant sources. The flavonoid reservoir 25 may also serve this function, that is, it may hold flavonoid material and lipophilic antioxidant material. The lipophilic antioxidant reservoir discharges lipophilic antioxidant material to the one of more, or all, of the hopper 15, mincer 17, press 19 means for separating a omega-3 fraction 21 and the storage vessel 23. Thus, the lipophilic antioxidant material is co-processed with the omega-3 source material through the receiving and through finished or semi-finished product.

The lipophilic anti-oxidants are selected from the group consisting of alpha-tocopherol (vitamin E), retinol (vitamin A) carotenoids and derivatives and derivatives and cholecalciferol (vitamin $D_3$) and derivatives. The lipophilic anti-oxidants may be derived from natural sources, for example, food sources rich in such compounds such as, by way of example without limitation, carrots and high value green leafy vegetables and marine sources like krill or Calanus fintnarchicus. Or, the anti-oxidants are obtained from non-natural sources.

In one aspect, the apparatus 11 further comprises means for forming a purified omega-3 fraction [not shown] which can be integral with or separate from storage vessel 23. The means for forming a purified omega-3 fraction is in communication with the flavonoid reservoir 25 to place flavonoids into the omega-3 fraction prior to or concurrent with the further purification and forming a purified omega-3 fraction.

The apparatus 11 is maintained at or operates at a temperature not exceeding 99 degrees centigrade and more preferably not greater than about 40 degrees centigrade by suitable heating and cooling equipment known in the art. Thus, the apparatus 11 defines a substantially closed, temperature controlled system, receiving source material in the form of materials having omega-3 fatty acids, flavonoids and lipophilic antioxidants and processing such materials through to a purified omega-3 fraction. Apparatus 11 is preferably sized to be mobile or capable of being carried on trucks receiving ships harvesting fish, marine animals, plants or algae for processing and making omega-3 fatty acid articles of manufacture and on ships themselves. Thus, close to the harvesting of source material for omega-3 fatty acids, the apparatus 11 produces articles of manufacture having little oxidation.

The hydrophilic flavonoids may preferentially partition into the water phase but remain present in the omega-3 fatty acid fraction in a concentration of between 250 to 10,000 ppm, or 500 to 2,000 ppm, or about 1,000 ppm. The lipophilic antioxidants may preferentially partition into the fatty acid phase and are present in the omega-3 fatty acid fraction in a concentration of between 250 to 10,000 ppm, or 500 to 2,000 ppm, or about 1,000 ppm.

The presence of the flavonoids and lipophilic antioxidants early in the processing of the source material for the omega-3 fatty acids prevents oxidation and spoilage of the omega-3 fatty acids.

Figure 3:
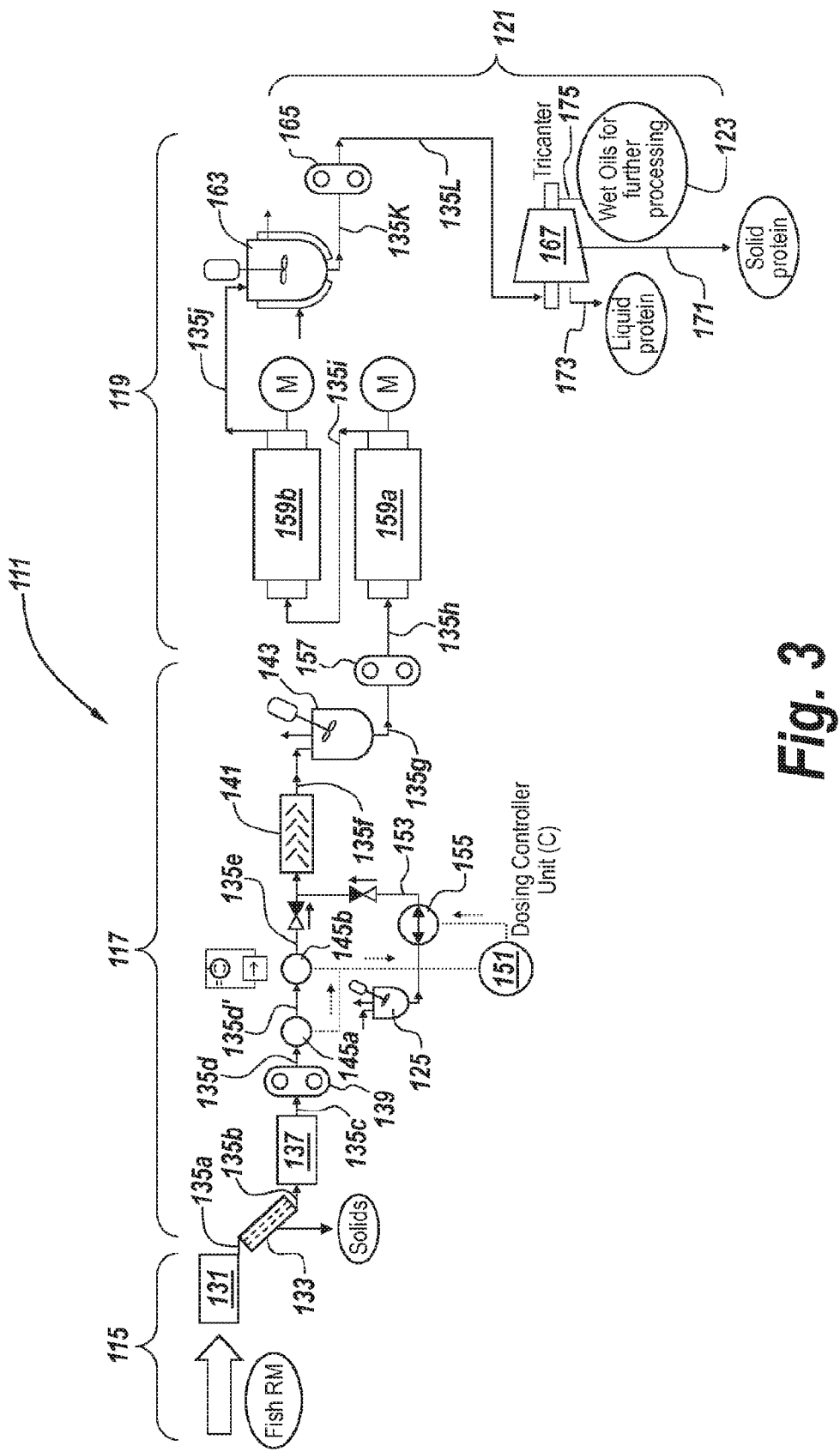

Turning now to FIG. 3, an apparatus for processing raw fish, generally designated by the numeral 111, is depicted. The apparatus 111 has following major elements, means for receiving sources of omega-3 fatty acids 115, means for forming a particulate omega-3 material 117, means for forming a omega-3 fraction 119, and means for separating the omega-3 fatty acid fraction 121, omega-3 fatty acid flavonoid storage means [not shown] and flavonoid reservoir 125.

The means for receiving sources of omega-3 fatty acids 115 is an assembly of parts comprising such parts and assembly [not shown] leading up to a fish hopper 131. The parts and assembly may comprise fish sorters and fish sizing means known in the art. The fish hopper 131 is in communication with means for forming a particulate omega-3 material 117 by means of a conduit 135*a*. Conduit 135*a* may further comprise augers, moving belts or turntables and other means for transporting fish or fish parts to means for forming a particulate omega-3 material 117.

Fish hopper is of a conventional design and available from numerous vendors. Fish raw material is conveyed from the fish hopper 131 to the deboner 133 via conduit 135*a*

Means for forming a particulate omega-3 material 117 is an assembly of parts comprising a deboner 133, a buffer hopper 137, first gear pump 139, static mixer 141 and buffer tank 143; linked by suitable conduits 135*a* through 135*g*. Deboner 133 and buffer hopper 137 are of conventional design and available from numerous vendors. Deboner 133 receives the fish material and minces the soft parts of the fish material and separates the solids and removes them from the process stream. Liquids are passed to buffer hopper 137 via conduit 135*b*. Buffer hopper 137 is a substantially closed vessel flushed with nitrogen. Buffer hopper 137 is in communication with first gear pump 139 via conduit 135*c*. First gear pump 139 powers the liquid through 135*d* to analytical element 145*a* and flow meter 145*b*, to be described in greater detail in the discussion that follows. A conduit 135*d'* is depicted between the analytical element 145*a* and the flow meter 145*b*. Those skilled in the arts will recognize that the relative positions of flow meter 145*b* and analytical element 145*a* can be reversed. And, flow meter 145*b* and analytical element 145*a* can be located in different parts of the flow stream or additional flow meters and analytical elements [not shown] can be placed in the flow stream. Flow meter 145*b*, static mixer 141 and buffer tank 143 are in fluid communication via conduits 135*e* and 135*f*.

Analytical element 145*a* and flow meter 145 are in signal communication with control means 151 as represented by dotted lines. The analytical element 145*a* monitors the water content and the total mass of the minced material. The flow meter 145*b* monitors the flow of omega-3 source material. As used herein, control means refers to computer, analog or digital type automated control system. Digital control systems comprise, by way of example, without limitation, computer processing units (CPUs) well known in the art, including integral CPUs and external CPUs of the type found in computers, laptops, mainframes, servers and hand-held computer devices, all well known in the art and available from numerous vendors. The term "signal communication" refers to data or command signals in the sense of to power or to send. For example, without limitation, such signal communication comprises wired together electronically, electro-magnetic signaling by means of radio, infra-red, optical, acoustic communication, WIFI and the like.

The flavonoid reservoir 125 is in communication with one or more of the means for receiving omega-3 source material 115, means for forming a particulate omega-3 material 117, means for forming an omega-3 fraction 119, and means for separating an omega-3 fraction 121. As depicted flavonoid reservoir 125 is in fluid communication with the means for forming a particulate omega-3 material via conduit 153 which is in communication with static mixer 141. A metering pump 155 is interposed into conduit 153 to precisely add the flavonoid material into static mixer 141. The source material for the flavonoids, for example, without limitation, leaves and other plant material from tea, moringa and/or cacao or extracts or powders or reconstituted liquids thereof is stored in flavonoid reservoir 125.

The metering pump 155 is in signal communication with control means 151 and is activated in response to the flow of omega-3 source material flowing past flow meter 145*b* and the content of the material as determined by analytical element 145*a*. Thus, the omega-3 source material flowing through the apparatus 111 is monitored and flavonoid source material is added to the flow, automatically, to levels set by the operator.

Flavonoid reservoir 125 may also receive and contain lipophilic antioxidants which are added simultaneously with flavonoids. Or, a separate reservoir for lipophilic antioxidants [not shown] and a separate metering pump [not shown] may be provided in communication with conduits and static mixer 141 or other parts and components of the apparatus 111. Such metering pump is in signal communication with the control means to add lipophilic antioxidants in response to the flow rate and the content of the liquids flowing through the apparatus 111. Thus, flavonoids and lipophilic antioxidants are added to the omega-3 source material early in the process and with precision to produce a consistent stable omega-3 fatty acid.

Buffer tank 143 is in communication with means for adjusting pH [not shown] and provides further mixing of the liquid containing particulates. Buffer tank 145, of the means for forming a particulate omega-3 material 117, is in fluid communication with means for forming an omega-3 fraction 119, via conduit 135*g* leading to second gear pump 157.

Means for forming an omega-3 fraction 119 comprises an assembly of parts including second gear pump 157, first controlled thermal tank 159*a* and second controlled thermal tank 159*b* and tricanter feed tank 163. Second gear pump 157 communicates with first controlled thermal tank via conduit 135*h*. First controlled thermal tank 159*a* and second controlled thermal tank 159*b* are in fluid communication via conduit 135*i*. The second controlled thermal tank 159*b* is in fluid communication with tricanter feed tank 163.

The second gear pump 157 propels the fluids through the means for forming an omega-3 fraction 119. The first controlled thermal tank 159*a* and second controlled thermal tank 159*b* adjust the temperature of the liquids to promote separation into fractions. The tricanter feed tank 163 maintains the fractions, with suitable mixing, until the fluids are received by means for separating an omega-3 fraction 121 via conduit 135K.

Means for separating an omega-3 fraction 121 comprises an assembly of parts comprising third gear pump 165 and tricanter 167. Tricanter feed tank is in fluid communication with third gear pump 165 via conduit 135*k*. Third gear pump 165 is in fluid communication with tricanter 167 via conduit 135*l*. Third gear pump 165 powers the fluids comprising an aqueous fraction and an oil fraction, which oil fraction comprises in whole or in part, omega-3 fatty acids, into the tricanter 167. Tricanter 167 separates the solids, aqueous fraction and oil fractions. The solid are removed via solids conduit 171. The aqueous fraction, rich in protein is removed via aqueous conduit 173. The oil fraction is removed via conduit 175 to means for storing or further processing an omega-3 fatty acid 123.

Means for storing an omega-3 fatty acid [not shown] may comprise individual product containers for finished omega-3 fatty acids or larger vessels holding omega-3 fatty acids for further processing and/or refinement. Such individual containers and larger vessels are known in the art and are omitted from this drawing for clarity.

The article of manufacture, an omega-3 fatty acid having flavonoids and lipophilic antioxidants is incorporated in a food products, or incorporated in a dosage forms for administration as a dietary and/or health supplement or as a medicament. For example, without limitation, the food product, dietary or health supplement, or medicament may comprise an omega-3 fatty acid oil for oral administration in a dosage of about 750 to 4000 mg. The omega-3 fatty acid oil is stable and essentially free of fish odors and free of fish tastes. The health benefit of omega-3 fatty acids can be obtained synergistically with other medicaments with the omega-3 fatty acid serving as a base for incorporating the medicaments in a suitable dosage form.

Figure 2:
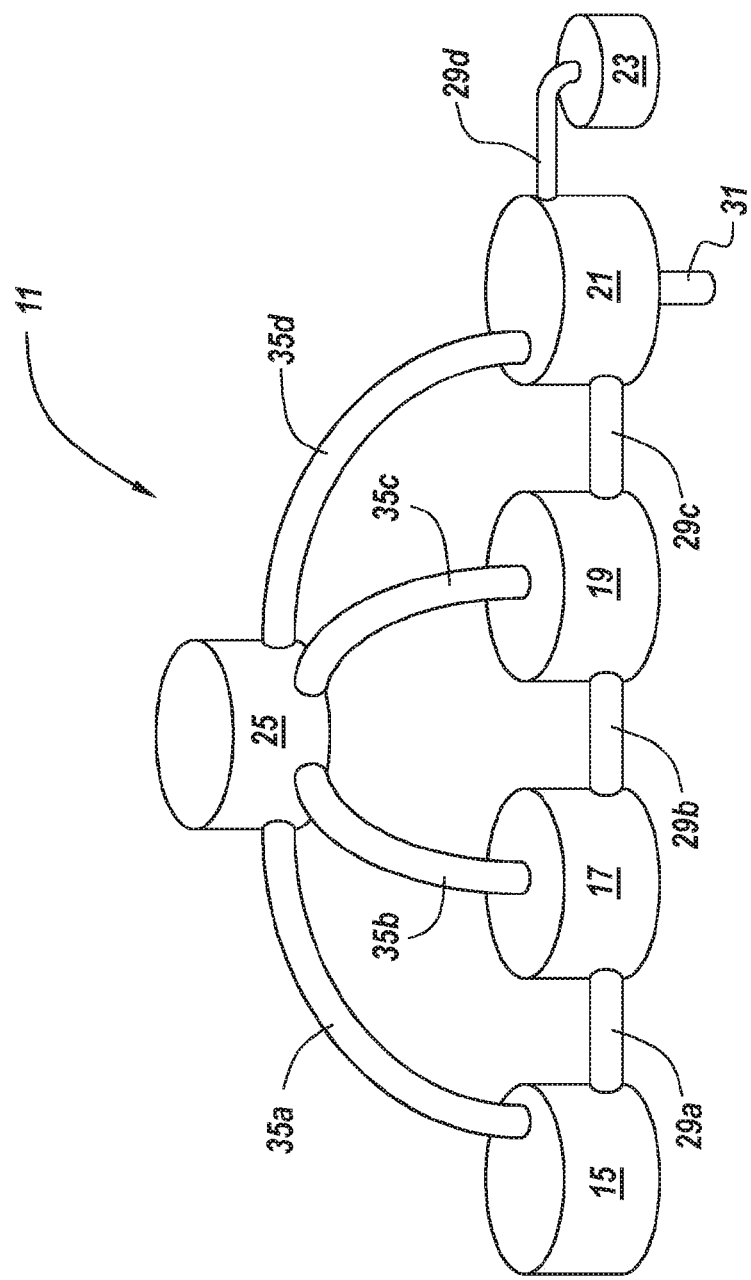
FIG. 2 depicts in schematic form, an apparatus for forming omega-3 fatty acid articles of manufacture of the present invention; and, FIG. 3 depicts in schematic form an apparatus for forming omega-3 fatty acid articles of manufacture of the present invention from fish materials.

Embodiments of the present method will now be described in detail with respect to a method of making an omega-3 article of manufacture with the apparatus 11, as depicted in FIG. 2. A source of omega-3 fatty acid having a aqueous component and an oil component, such as fish and fish parts, is placed in hopper 15 with one or more sources of flavonoids from flavonoid reservoir 25 and one or more sources of lipophilic antioxidants from an antioxidant reservoir [not shown]. By way of example without limitation, a source of flavonoids, leaves, powders and extracts of green tea, cacao and moringa, is combined with the source of omega-3 fatty acids, for example, combined with whole fish, fish parts plant or algal materials, and source material for lipophilic antioxidants, to form an admixture.

The admixture is passed to the mincer 17 and rendered into small particles by means of mincing or grinding to form a particulate admixture. The particulate admixture is passed to the press 19 and the particulate admixture pressed to produce a liquid having oil and water components. The liquid having oil and water components is passed to the separation vessel 21 to form an oil fraction and a water fraction. Each of these steps is potentially supplemented with additional flavonoid material, melatonin and lipophilic antioxidants.

The omega-3 fatty acid fraction is passed to storage vessel 23 as a finished product or subjected to further refining and processing.

The flavonoids and/or melatonin stabilize and prevent oxidation of the omega-3 fatty acid. The hydrophilic flavonoids are present in the article of manufacture in a concentration of between 250 to 10,000 ppm, or 500 to 2,000 ppm, or about 1,000 ppm. The resulting article of manufacture has lipophilic anti-oxidants present in a concentration of between 250 to 10,000 ppm, or 500 to 2,000 ppm, or about 1,000 ppm. One preferred standard concentration of melatonin corresponds to an amount equal to or greater than melatonin levels in cod liver oil. The flavonoids, melatonin and/or lipophilic antioxidants are present throughout the process and prevent oxidation of the omega-3 fatty acids from the earliest point of processing.

Thus, embodiments of the present invention have been described in detail with the understanding that such description is directed to preferred embodiments and what is now considered to be the best mode of practicing the invention. However, embodiments of the present invention are capable of modification and alteration without departing from the teaching herein, such that the present invention should not be limited to the details herein but should encompass the subject matter of the claims that follow and their equivalents.

The invention claimed is:

1. An apparatus for forming an omega-3 article of manufacture from an omega-3 source material, an omega-3 fraction, and a separated omega-3 fraction comprising:
   means for forming a particulate omega-3 material,
   means for forming an omega-3 fraction,
   means for separating an omega-3 fraction,
   one or more flavonoid reservoirs and one or more melatonin reservoirs, said one or more flavonoid reservoirs and one or more melatonin reservoirs being in communication with one or more of said means for forming a particulate omega-3 material, means for forming an omega-3 fraction, and means for separating an omega-3 fraction;
   means to place flavonoids and a concentration of melatonin in at least one of said means for forming a particulate omega-3 material, said means for forming an omega-3 fraction, and said means for separating an omega-3 fraction; and
   means for monitoring and adjusting the concentration of melatonin placed in one or more of the group comprising the omega-3 source material, the particulate omega-3 material, the omega-3 fraction, and the separated omega-3 fraction by the means to place flavonoids and a concentration of melatonin,
   wherein the means for forming a particulate omega-3 material allows said omega-3 source material, said omega-3 fraction and said separated omega-3 fraction to be co-processed with said flavonoids and the concentration of melatonin.

2. The apparatus of claim 1 wherein said means are maintained at a temperature not exceeding 99 degrees centigrade.

3. The apparatus of claim 1 wherein said means for forming a particulate omega-3 material is in communication with said means for forming a omega-3 fraction to pass a particulate omega-3 material to said means for forming an omega-3 fraction, and said means for forming an omega-3 fraction is in communication with said means for separating an omega-3 fraction to pass an omega-3 fraction to said means for separating an omega-3 fraction.

4. The apparatus of claim 1 wherein apparatus performs steps in a process to form a separated omega-3 fraction in a continuous manner.

5. The apparatus of claim 1 wherein said means are located on a water vessel which procures sources of omega-3 material from natural sources.

6. The apparatus of claim 1 wherein said means are mounted on a truck bed.

7. The apparatus of claim 1 wherein said means are mounted on a water vessel.

8. The apparatus of claim 1, wherein the means to place flavonoids and the concentration of melatonin places flavonoids and the concentration of melatonin into the omega-3 fraction prior to or concurrent with forming a particulate omega-3 material.

9. The apparatus of claim 1, wherein the means for monitoring and adjusting the concentration of melatonin regulates to a concentration of melatonin that is substantially equal to or greater than melatonin levels in cod liver oil.

10. An apparatus for forming an omega-3 article of manufacture from an omega-3 source material, an omega-3 fraction, and a separated omega-3 fraction comprising:
   means for forming a particulate omega-3 material,
   means for forming an omega-3 fraction,
   means for separating an omega-3 fraction,
   one or more melatonin reservoirs in communication with one or more of said means for forming a particulate omega-3 material, means for forming an omega-3 fraction, and means for separating an omega-3 fraction;
   means to place a concentration of melatonin in at least one of said means for forming a particulate omega-3 material, means for forming an omega-3 fraction, and means for separating an omega-3 fraction; and means for monitoring and adjusting the concentration of melatonin placed in one or more of the group comprising the omega-3 source material, the particulate omega-3 material, the omega-3 fraction, and the separated omega-3 fraction, wherein the means for forming a particulate omega-3 material allows said omega-3 source material, said omega-3 fraction, and said separated omega-3 fraction to be co-processed with said concentration of melatonin.

11. The apparatus of claim 10 further comprising:
one or more flavonoid reservoirs in at least one of said means for forming a particulate omega-3 material, means for forming an omega-3 fraction, and means for separating an omega-3 fraction; and
means to place flavonoids in at least one of said means for forming a particulate omega-3 material, means for forming an omega-3 fraction, and means for separating an omega-3 fraction,
wherein the means for forming a particulate omega-3 material further allows said omega-3 source material, said omega-3 fraction, and said separated omega-3 fraction to be co-processed with said flavonoids.

12. The apparatus of claim 10 wherein said means are maintained at a temperature not exceeding 99 degrees centigrade.

13. The apparatus of claim 10 wherein said means for forming a particulate omega-3 material is in communication with said means for forming a omega-3 fraction to pass a particulate omega-3 material to said means for forming an omega-3 fraction and said means for forming an omega-3 fraction is in communication with said means for separating an omega-3 fraction to pass an omega-3 fraction to said means for separating an omega-3 fraction.

14. The apparatus of claim 10 wherein apparatus performs steps in a process to form a separated omega-3 fraction in a continuous manner.

15. The apparatus of claim 10 wherein said means are located on a water vessel which procures sources of omega-3 material from natural sources.

16. The apparatus of claim 10 wherein said means are mounted on a truck bed.

17. The apparatus of claim 10, wherein the means to place the concentration of melatonin places the concentration of melatonin into the omega-3 fraction prior to or concurrent with forming a particulate omega-3 material.

18. The apparatus of claim 10, wherein the means for monitoring and adjusting the concentration of melatonin regulates to a concentration of melatonin that is substantially equal to or greater than melatonin levels in cod liver oil.

* * * * *